United States Patent [19]

Moore et al.

[11] Patent Number: 5,290,537
[45] Date of Patent: Mar. 1, 1994

[54] COMPOSITIONS FOR MAGNETIC RESONANCE IMAGING

[75] Inventors: Dennis A. Moore, Ferguson; Rebecca A. Wallace, Manchester, both of Mo.

[73] Assignee: Mallinckrodt Medical, Inc., St. Louis, Mo.

[21] Appl. No.: 16,630

[22] Filed: Feb. 12, 1993

Related U.S. Application Data

[62] Division of Ser. No. 875,503, Apr. 29, 1992, Pat. No. 5,208,375, which is a division of Ser. No. 724,653, Jul. 2, 1991, Pat. No. 5,138,040.

[51] Int. Cl.$^5$ .............................................. A61K 49/00
[52] U.S. Cl. ........................................ 424/9; 128/653.4
[58] Field of Search ................ 424/9; 556/50, 55, 56, 556/44, 62, 63, 115, 116, 148; 514/499, 501, 505, 740; 534/14, 15, 16; 564/197, 511

[56] References Cited

U.S. PATENT DOCUMENTS

| | | | |
|---|---|---|---|
| 2,523,275 | 9/1950 | Bruce et al. | 564/197 |
| 2,856,427 | 10/1958 | Bruce et al. | 564/197 |
| 4,022,606 | 5/1977 | Conrad et al. | 71/67 X |
| 4,647,447 | 3/1987 | Gries et al. | 424/9 |
| 4,687,659 | 8/1987 | Quay | 424/9 |
| 4,694,081 | 9/1987 | Miller et al. | 544/385 |
| 4,826,673 | 5/1989 | Dean et al. | 424/9 |
| 5,137,711 | 8/1992 | Weber et al. | 424/9 |

FOREIGN PATENT DOCUMENTS

3316755 6/1987 Japan.

*Primary Examiner*—Robert L. Stoll
*Assistant Examiner*—Lara E. Chapman
*Attorney, Agent, or Firm*—Rita D. Vacca; Brian K. Stierwalt

[57] ABSTRACT

Methods and compositions for enhancing magnetic resonance imaging in at least a portion of a warm-blooded animal.

6 Claims, No Drawings

COMPOSITIONS FOR MAGNETIC RESONANCE IMAGING

This is a division of application Ser. No. 07/875,503, filed Apr. 29, 1992. Application Ser. No. 07/875,503 is a divisional application of application Ser. No. 07/724,653 now U.S. Pat. No. 5,208,375.

BACKGROUND OF THE INVENTION

This invention relates to magnetic resonance imaging agents, and more particularly to methods and compositions for enhancing magnetic resonance imaging.

The recently developed technique of magnetic resonance imaging (MRI) encompasses the detection of certain atomic nuclei utilizing magnetic fields and radio-frequency radiation. It is similar in some respects to X-ray computed tomography (CT) in providing a cross-sectional display of the body organ anatomy with excellent resolution of soft tissue detail. As currently used, the images produced constitute a map of the distribution density of protons and/or the relaxation times in organs and tissues. The technique of MRI is advantageously non-invasive as it avoids the use of ionizing radiation.

While the phenomenon of MRI was discovered in 1945, it is only relatively recently that it has found application as a means of mapping the internal structure of the body as a result of the original suggestion of Lauterbur (Nature, 242, 190-191 (1973)). The fundamental lack of any known hazard associated with the level of the magnetic and radio-frequency fields that are employed renders it possible to make repeated scans on vulnerable individuals. Additionally, any scan plane can readily be selected, including transverse, coronal and sagittal sections.

In an MRI experiment, the nuclei under study in a sample (e.g. protons) are irradiated with the appropriate radio-frequency (RF) energy in a controlled gradient magnetic field. These nuclei, as they relax, subsequently emit RF energy at a sharp resonance frequency. The resonance frequency of the nuclei depends on the applied magnetic field.

According to known principles, nuclei with appropriate spin when placed in an applied magnetic field (B, expressed generally in units of gauss or Tesla ($10^4$ gauss)) align in the direction of the field. In the case of protons, these nuclei precess at a frequency, F, of 42.6 MHz at a field strength of 1 Tesla. At this frequency, an RF pulse of radiation will excite the nuclei and can be considered to tip the net magnetization out of the field direction, the extend of this rotation being determined by the pulse, duration and energy. After the RF pulse, the nuclei "relax" or return to equilibrium with the magnetic field, emitting radiation at the resonant frequency. The decay of the emitted radiation is characterized by two relaxation times, i.e., $T_1$, the spin-lattice relaxation time or longitudinal relaxation time, that is, the time taken by the nuclei to return to equilibrium along the direction of the externally applied magnetic field, and $T_2$, the spin-spin relaxation time associated with the dephasing of the initially coherent precession of individual proton spins. These relaxation times have been established for various fluids, organs and tissues in different species of mammals.

In MRI, scanning planes and sliced thicknesses can be selected. This selection permits high quality transverse, coronal and saggital images to be obtained directly. The absence of any moving parts in MRI equipment promotes a high reliability. It is believed that MRI has a greater potential than CT for the selective examination of tissue characteristics. The reason for this being that in CT, X-ray attenuation and coefficients alone determine image contrast, whereas at least four separate variables ($T_1$, $T_2$, proton density and flow) may contribute to the MRI signal. For example, it has been shown (Damadian, Science, 171, 1151 (1971)) that the values of the $T_1$ and $T_2$ relaxation in tissues are generally longer by about a factor of two (2) in excised specimens of neoplastic tissue compared with the host tissue.

By reason of its sensitivity to subtle physiochemical differences between organs and/or tissues, it is believed that MRI may be capable of differentiating different tissue types and in detecting diseases which induce physicochemical changes that may not be detected by X-Ray or CT which are only sensitive to differences in the electron density of tissue.

As noted above, two of the principal imaging parameters are the relaxation times, $T_1$ and $T_2$. For protons (or other appropriate nuclei), these relaxation times are influenced by the environment of the nuclei (e.g., viscosity, temperature, and the like). These two relaxation phenomena are essentially mechanisms whereby the initially imparted radio-frequency energy is dissipated to the surrounding environment. The rate of this energy loss or relaxation can be influenced by certain other nuclei which are paramagnetic. Chemical compounds incorporating these paramagnetic nuclei may substantially alter the $T_1$ and $T_2$ values for nearby protons. The extent of the paramagnetic effect of the given chemical compound is a function of the environment within which it finds itself.

In general, paramagnetic ions of elements with an atomic number of 21 to 29, 42 to 44 and 58 to 70 have been found effective as MRI contrasting agents. Suitable such ions include chromium (III), manganese (II), manganese (III), iron (III), iron (II), cobalt (II), nickel (II), copper (II), praseodymium (III), neodymium (III), samarium (III) and ytterbium (III). Because of their very strong magnetic moments, gadolinium (III), terbium (III), dysprosium (III), holmium (III) and erbium (III) are preferred. Gadolinium (III) ions have been particularly preferred as MRI contrasting agents.

Typically, the divalent and trivalent paramagnetic ions have been administered in the form of complexes with organic complexing agents. Such complexes provide the paramagnetic ions in a soluble, non-toxic form, and facilitate their rapid clearance from the body following the imaging procedure. Gries, et al., U.S. Pat. No. 4,647,447, disclosed complexes of various paramagnetic ions with conventional aminocarboxylic acid complexing agents. A preferred complex disclosed by Gries, et al., is a complex of gadolinium (III) with diethylenetriaminepentaacetic acid ("DTPA"). DTPA is represented by the formula:

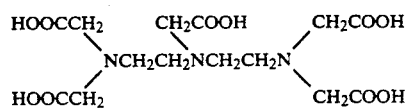

Paramagnetic ions, such as gadolinium (III), have been found to form strong complexes with other polyaminocarboxylic acids such as, cyclohexanediaminetetraacetic acid ("CDTA") (not illustrated), ethylenediaminetetraacetic acid ("EDTA") represented by the formula:

and tetraazacyclododecane-N,N',N''', N''''-tetraacetic acid ("DOTA") represented by the formula:

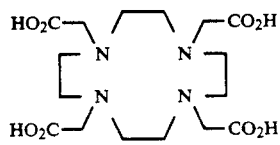

These complexes do not dissociate substantially in physiological aqueous fluids. The complexes have a net charge of −1 or −2, and generally are administered as soluble salts. Typical such salts are the sodium and Nmethylglucamine salts.

The administration of ionizable salts is attended by certain disadvantages. These salts can raise the in vivo ion concentration and cause localized disturbances in osmolality, which in turn, can lead to edema and other undesirable reactions.

Efforts have been made to design non-ionic paramagnetic ion complexes. In general, this goal has been achieved by converting one or more of the free carboxylic acid groups of the polyamino acid type ligands such as EDTA or DTPA to neutral, non-ionizable groups. For example, S. C. Quay, in U.S. Pat. Nos. 4,687,658 and 4,687,659, discloses alkylester and alkylamide derivatives respectively, of DTPA complexes. Similarly, published Dean et al., U.S. Pat. No. 4,826,673 discloses mono- and polyhydroxyalkylamide derivatives of DTPA and their use as complexing agents for paramagnetic ions.

The nature of the derivative used to convert carboxylic acid groups to non-ionic groups can have a significant impact on solubility. For example, derivatizing the carboxylic acid groups with hydrophobic alkylamide groups substantially decreases the water solubility of the complex. The solubility of the complex in physiological fluids can, in turn, affect the tissue selectivity of the complex. Hydrophilic complexes tend to concentrate in the interstitial fluids, whereas hydrophobic complexes tend to associate with cells. Thus, differences in hydrophilicity can lead to different applications of the compounds. See, for example, Weinmann, et al., AJR, 142, 679 (Mar. 1984) and Brasch, et al., AJR, 142, 625 (Mar. 1984).

Thus, a need continues to exist for new and structurally diverse ionic and non-ionic complexes of paramagnetic ions for use as MRI agents. A further need also exists in the art to develop highly stable complexes with good relaxivity and low osmolar characteristics.

SUMMARY OF THE INVENTION

The present invention provides novel complexing agents and complexes of complexing agents with paramagnetic ions for use in MRI. The complexes are represented by the two following general formulas:

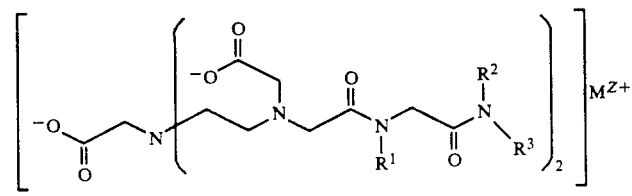

Formula I

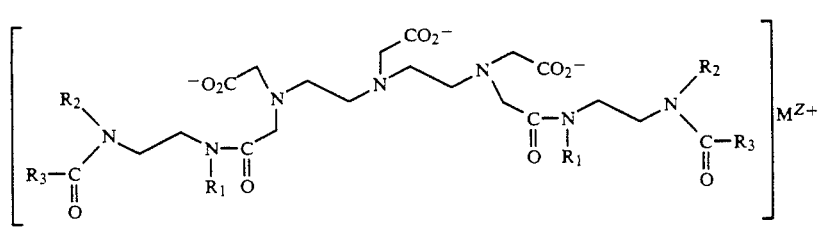

Formula II wherein the $R_1$, $R_2$ and $R_3$ groups may be the same or different selected from the group consisting of hydrogen, $C_{1-6}$, alkyl such as for example methyl or ethyl wherein methyl is preferable to minimize lipophilicity, $C_{1-6}$ alkoxy -such as for example methoxy or ethoxy, $C_{1-8}$ mono- or polyhydroxyalkyl -such as for example hydroxymethyl or dihydroxypropyl wherein dihydroxypropyl is preferred to enhance water solubility, $C_{1-6}$ alkylalkoxy -such as for example methylmethoxy, and $C_{1-6}$ alkoxyalkyl - such as for example methoxymethyl or methoxyethyl wherein methoxymethyl is preferred to reduce lipophilicity. Examples of such substituents include but are not limited to:

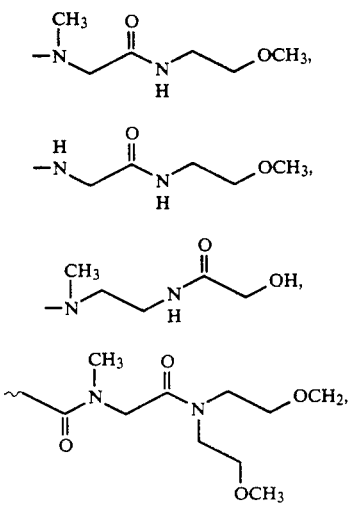

-continued

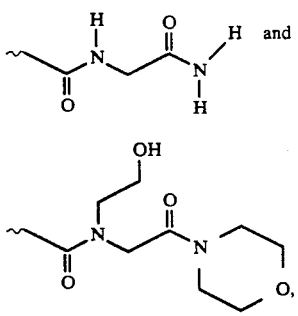

wherein M²⁺ in the formulas above is a paramagnetic ion selected from a group of elements having atomic numbers of 21–25, 27–29, 42–44, and 58–70 and a valence, z, of 2+ or 3+.

Also, disclosed is a diagnostic composition and a method of performing a MRI diagnostic procedure which involves administering to a warm-blooded animal an effective amount of the above-described complex and then exposing the warm-blooded animal to a MRI procedure, thereby imaging at least a portion of the body of the warmblooded animal.

DETAILED DESCRIPTION OF THE INVENTION

The complexing agents employed in this invention are derivatives of the well-known chelating agents such as DTPA, EDTA, CDTA or DOTA. In these derivatives, free carboxylic acid groups (those not involved in the formation of coordination bonds with the paramagnetic ion) are converted to amide groups. Thus, for example, if the paramagnetic ion is trivalent, two of the carboxylic acid groups of DTPA will be derivatized to the amide form. Likewise, if the paramagnetic ion is divalent, three of the carboxylic acid groups of DTPA will be derivatized to the amide form. When reacted with a divalent or trivalent paramagnetic ion, the resulting complexes are substantially non-ionic and neutral. The same principle would be true if other chelating agents such as EDTA, CDTA or DOTA were to be used.

The amide derivatives of chelating agents such as DTPA, EDTA, CDTA or DOTA are prepared in a conventional manner. In general, they are prepared by reacting a stoichiometric amount of a compound having an amine group of the general formula

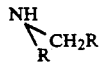

with a reactive derivative of a chelating agent under amide-forming conditions. Such reactive derivatives include, for example, anhydrides, mixed anhydrides and acid chlorides.

In one embodiment, the reactions are conducted in an organic solvent at an elevated temperature. Suitable solvents include those in which the reactants are sufficiently soluble and which are substantially unreactive with the reactants ana products. Lower aliphatic alcohols, ketone, ethers, esters, chlorinated hydrocarbons, benzene, toluene, xylene, lower aliphatic hydrocarbons, and the like may be advantageously used as reaction solvents. Examples of such solvents are methanol, ethanol, propanol, butanol, pentenol, acetone, methylethylketone, diethylketone, methylacetate, ethylacetate, chloroform, methylenechloride, dichloroethane, hexane, heptane, octane, decane, and the like. If an acid chloride is used as a starting material, then the reaction solvent advantageously is one which does not contain reactive functional groups, such as hydroxyl groups, as these solvents can react with the acid chlorides, thus producing unwanted byproducts.

The reaction temperature may vary widely, depending upon the starting materials employed, the nature of the reaction solvent and other reaction conditions. Such reaction temperatures may range, for example, from about 0° C. to about 150° C. preferably from about 30° C. to about 70° C.

Following the reaction of the reactive derivative with the amine, any remaining anhydride or acid chloride groups can be hydrolyzed to the carboxylic groups by adding a stoichiometric excess of water to the reaction mixture and heating for a short time.

The resulting DTPA, EDTA, CDTA or DOTA alkoxyalkylamide is recovered from the reaction mixture by conventional procedures. For example, the product may be precipitated by adding a precipitating solvent to the reaction mixture and recovered by filtration or centrifugation.

In the amine formula

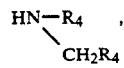

following the above process, R₄ may be hydrogen, C₁₋₆ alkyl -such as for example methyl or ethyl wherein methyl is preferable to reduce lipophilicity, C₁₋₆ alkoxy -such as for example methoxy or ethoxy wherein methoxy is preferable to reduce lipophilicity, C₁₋₆ mono- or poly- hydroxyalkyl -such as for example hydroxymethyl or dihydroxypropyl wherein dihydroxypropyl is preferable to enhance water solubility, amine -such as for example amino or methylamino, or C acylaminoalkyl -such as for example acetylaminomethyl or propionylaminomethyl, wherein each of the acyl and alkyl groups contain one (1) to six (6) carbon atoms.

The paramagnetic ion is then combined with the above isolated alkoxyalkyl amide derivative under complex-forming conditions. In general, any of the paramagnetic ions referred to above can be employed in making the complexes of this invention. The complexes can conveniently be prepared by mixing a suitable oxide or salt to the paramagnetic ion with the complexing agent in aqueous solution. To assure complete complex formation, a slight stoichiometric excess of the complexing agent may be used. In addition, an elevated temperature, e.g., ranging from about 20° C. to about 100° C., preferably from about 40° C. to about 80° C., may be employed to insure complete complex formation. Generally, complete complex formation will occur within a period from a few minutes to a few hours after mixing. The complex may be recovered by precipitation using a precipitating solvent such as acetone, and further purified by crystallization, if desired.

The novel complexes of this invention can be formulated into diagnostic compositions for enteral or parenteral administration. These compositions contain an effective amount of the paramagnetic ion complex along with conventional pharmaceutical carriers and excipients appropriate for the type of administration contemplated. For example, parenteral formulation advantageously contain a sterile aqueous solution or suspension of from about 0.05 to 1.0M of a paramagnetic ion complex according to this invention. Preferred parental formulations have a concentration of paramagnetic ion complex of 0.1M to 0.5M. Such solutions also may contain pharmaceutically acceptable buffers and, optionally, electrolytes such as sodium chloride. Advantageously, the compositions may further contain physiologically acceptable non-toxic cations in the form of a gluconate, chloride or other suitable organic or inorganic salts, including suitable soluble complexes with a chelate/ligand to enhance safety. Such chelates/ligands include the ligands set forth above used to complex paramagnetic and/or heavy metals to provide the complex formulations of this invention. Advantageously, the cation-ligand complex is provided in amounts ranging from about 0.001 Mol percent to about 15 Mol percent excess, of the ligand-metal complex. Examples of such physiologically acceptable non-toxic cations include sodium ions, calcium ions, magnesium ions, copper ions, zinc ions and the like including mixtures thereto. Calcium ions are preferred.

Parenteral compositions may be injected directly or mixed with a large volume parenteral composition for systemic administration.

Formulations for enteral administration may vary widely, as is well-known in the art. In general, such formulations are ligands which include an effective amount of the paramagnetic ion complex in aqueous solution or suspension. Such enteral compositions may optionally include buffers, surfactants, thixotropic agents, and the like. Compositions for oral administration may also contain flavoring agents and other ingredients for enhancing their organoleptic qualities.

The diagnostic compositions are administered in doses effective to achieve the desired enhancement of the NMR image. Such doses may vary widely, depending upon the particular paramagnetic ion complex employed, the organs or tissues which are the subject of the imaging procedure, the NMR imaging equipment being used, etc. In general, parenteral dosages will range from about 0.01 to about 1.0 MMol of paramagnetic ion complex per kilogram of patient body weight. Preferred parenteral dosage range from about 0.05 to about 0.5 MMol of the paramagnetic ion complex per kilograin of patient body weight. Enteral dosages generally range from about 0.5 to about 100 MMol, preferably from about 1.0 to about 20 MMol of paramagnetic ion complex per kilogram of patient body weight.

The novel MRI contrasting agents of this invention possess a unique combination of desirable features. The paramagnetic ion complexes exhibit a high solubility in physiological fluids, notwithstanding their substantially non-ionic character. This high solubility allows the preparation of concentrated solutions, thus minimizing the amount of fluid required to be administered. The non-ionic character of the complex also reduces the osmolality of the diagnostic compositions, thus preventing undesired edema and other side effects.

The diagnostic compositions of this invention are used in the conventional manner. Compositions may be administered in a sufficient amount to provide adequate visualization, to a warm-blooded animal either systemically or locally to an organ or tissues to be imaged, and the animal then subjected to the MRI procedure. The compositions have been found to enhance the magnetic resonance images obtained by these procedures. In addition to their utility and magnetic resonance imaging procedures, the complexing agents of this invention may also be employed for delivery of radiopharmaceuticals or heavy metals for X-Ray contrast into the body. The invention is further illustrated by the following examples, which are not intended to be limiting.

EXAMPLE 1

Preparation of
{(Aqua(N,N''-bis(N''''-2-methoxyethylcarbamoylmethyl-N'''-methylcarbamoylmethyl)diethylene-triamine-N,N',N''-triacetate))gadoliniuln(III) (4)

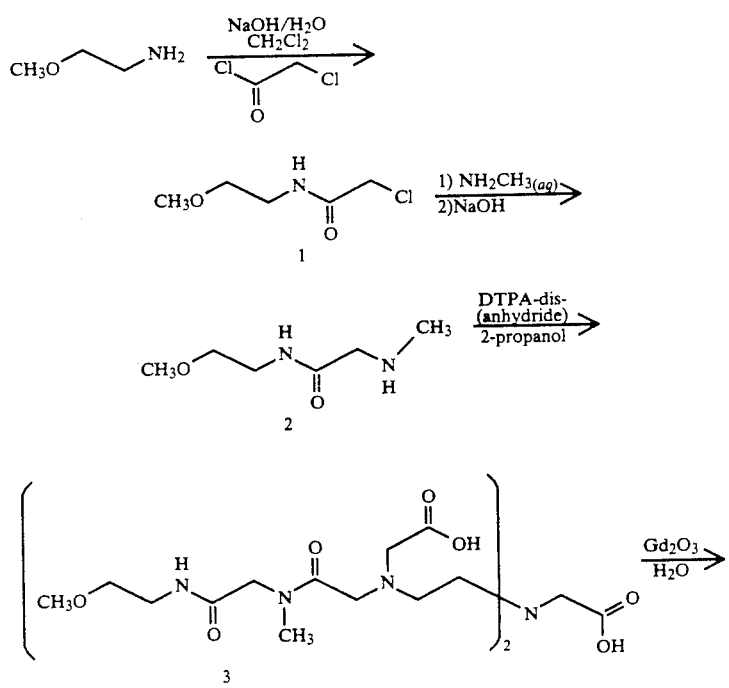

-continued

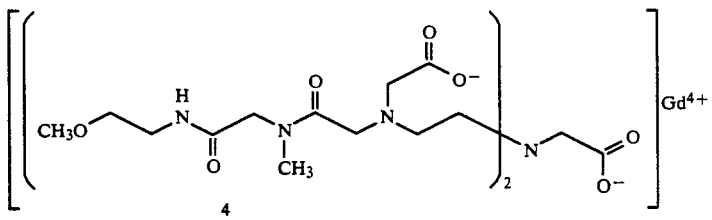

The first step is a modified Schotten-Baumann acetylation of 2-methoxy-ethyl amine. The chloroamide, 1, is readily purified by vacuum distillation (1 torr, 58° C.). Next, methylamine is N-alkylated with the chloroamide. The resulting N-methylglycine(2-methoxyethylamide), 2, is also purified by vacuum distillation (1 torr, 28° C.). Reaction of the glycinamide with diethylenetriaminepentaacetic dianhydride in 2-propanol gives the desired bis(amide) of DTPA, 3. Complexation of the ligand with gadolinium gives the complex, 4. The complex is purified by reverse phase flash chromatography.

Experimental

A) Chloro(N-(2-methoxyethyl))acetamide, (1)

In a three-necked 2L round bottom flask fitted with two 500 mL addition funnels, containing 56.4g (39.8 mL, 0.50 mole) chloroacetyl chloride in 400 mL dichloromethane and 20g (0.50 mole) sodium hydroxide in 400 mL water, respectively, and a water-cooled condenser, was placed 35.7g (41.3 mL, 0.48 mole) 2-methoxyethylamine, 100 mL water, 100 mL dichloro-methane. The reaction vessel was cooled to 0° C. by a salt-ice bath. The organic and aqueous solutions were allowed to add slowly, ~0.25 mL per minute, to the reaction mixture. During the addition the pH of the water phase of the reaction was monitored and the rate of addition of the alkali solution adjusted so as to maintain pH=12. When the addition was complete, the mixture was allowed to warm to room temperature and stir overnight. The organic layer was removed by siphon and dried with magnesium sulfate for four hours. The mixture was filtered through #4 filter paper on a large Buchner funnel and the sulfate washed with 2×100 mL fresh dichloromethane. The combined filtrates were then placed in 2L round bottomed flask and the mixture distilled at 1 torr. Fractions collected from 55° C. to 60° C. were combined and analyzed by NMR. Yield 31.1g (43% based on starting 2-methoxyethylamine). TLC (silica on glass, 2% methanol in dichloromethane) $R_f$=0.40. $^1H(\delta,CDCl_3)$ 3.28(s,3H), 3.40(m,4H), 3.97(s,2H), 6.92(br, 1H). $^{13}C\{^1H\}$ ($\delta$, $CDCl_3$) 39.27, 42.32, 58.60, 70.54, 166.22.

B) N'-(2-methoxyethyl)-N-methylglycinamide, (2)

To a 1L round bottom flask, fitted with reflux condenser and charged with 500 mL 40% w/w aqueous methylamine, was added, with stirring, 31.1 g (0.21 mole) chloroamide, 1. The mixture was heated to 35° C. and stirred overnight. To the mixture was added 8.8g (0.22 mole) sodium hydroxide. The mixture was distilled at room pressure and the fraction boiling from 89° C. to 98° C. The crude distillate was dried with magnesium sulfate and distilled again giving a clear colorless oil. Yield 13.9g (45% based on starting chloroamide, 1). TLC (silica on glass, 154 concentrated ammonium hydroxide in methanol) $R_f$=0.35. $^1H(\delta, CDCl_3)$ 1.38 (br, 1H), 2.32 (s,3H), 3.14 (s,2H), 3.26(s,3H), 3.37 (m,4H), 7.35 (br,1H). $^{13}C\{^1H\}(\delta,CDCl_3)$ 36.28, 38.39, 54.24, 58.53, 71.13, 171.62.

C) N,N''-bis(N''''-2-methoxyethylcarbamoylmethyl-N'''-methylcarbamoylmethyl)diethylenetriamine-N,N',N''-triacetic acid, (3)

A 2L round bottom flask was charged with 13.9g (0.095 mole) glycinamide, 2, 17.0 g (0.047 mole) diethylenetriaminepentaacetic dianhydride and 1L 2-propanol. The mixture was heated to 60° C. and allowed to stir overnight. The mixture was cooled to room temperature, transferred, in 1L lots, to a 2L recovery flask and the solvent removed by means of a rotary-evaporater (water aspirator). To residue was added 11 distilled/deionized water, and the mixture filtered to remove diethylenetriaminepentaacetic acid. The water was removed by rotary evaporation giving an orange glass. Yield 34 g (100%=30.9 g based on starting anhydride). Typically, the ligand is used "as is" for complexometric reactions. A small sample was purified by reverse phase flash column chromatography. IR(cm$^{-1}$) C-O 1724 (m,sh), 1659 (vs,). Anal. Calc. %C 48.07, %H 7.29, %N 15.09. Found %C 47.77, %H 7.04, %N 15.39.

D) (Aqua(N,N''-bis(N''''-2-methoxyethylcarbamoylmethyl-N'''-methylcarbamoylmethyl)diethylenetriamine -N,N',N''-triacetate))gadolinium(III), (4)

A 1L round bottom flask was charged with 34 g (assuming 30.9 g, 0.048 mole anhydrous ligand present) crude ligand, 3, 8.69 (0.024 mole) gadolinium oxide and 500 mL water. The mixture was heated to gentle reflux and stirred overnight. The slightly turbid yellow mixture was filtered (0.42 micron) and concentrated to 50 mL by rotary evaporator with a water aspirator. The thick clear solution was applied to a 5×35 cm column loaded with YMC C-18 reverse phase packing. The column was eluted with water. Those fractions containing >98% pure complex, by HPLC with uv detector at 215 nm, were combined, concentrated, filtered (0.42 micron) and evaporated to give a clear, colorless powder. Yield 20.5g (50% based on starting ligand, 3.) IR (cm$^{-1}$) C=0 1676 (s,sh), 1620 (vs). Anal. Calc. for $C_{26}H_{46}N_7O_{12}\cdot3H_2O$ %C 36.31, %H 6.09, %N 11.40, %Gd 18.29. Found %C 36.04, %H 5.90, %N 11.12, %Gd 17.79. Karl Fisher water calc. 5.91%, found 6.30%.

The mouse i.v. LD$_{50}$ value of a 0.5M solution of (Aqua(N,N''I-bis(N''''-2-methoxyethylcarbamoylmethyl-N'''-methylcarbamoylmethyl) diethylenetriamine-N,N',N$\Delta$-triacetate))gadolinium(III) was determined to be 32.5 mmol/kg (confidence limit of 27.3-38.8 mmol/kg) and the relaxivity rates (mmol$^{-1}$sec$^{-1}$) were obtained using the Bruker NMR Minispec (20 MHz) spectrometer at 40° C. in both sterile water for injection

EXAMPLE 2

A) N'-(2-Hydroxyethyl)-N-(2-hydroxyethyl)-glycinamide(6)

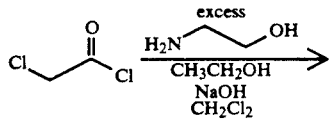

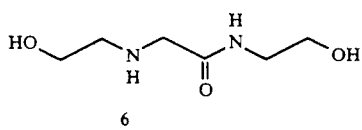

Chloroacetyl chloride (56.7 g, 0.5 mol) was added dropwise to ethanolamine (160 g, 2.6 mol) in methylene chloride (150 ml) at ice water temperature and the mixture was allowed to stir at this temperature for 60 minutes and then at room temperature for 60 minutes. The solvent was removed by rotary evaporation. Ethanol (150 ml) was used to dissolve the residue. Sodium hydroxide pellets (40.0 g, 1.0 mol) were added to the mixture. The mixture was stirred at room temperature for 2 hours. Sodium chloride was removed by filtration. The filtrate was rotary evaporated under reduced pressure (<0.5 torr) to remove the ethanol, water, and ethanolamine. The crude product (72.3 g, 89%) was purified by C-18 chromatography using deionized water for elution. After the water was removed, the purified product was a colorless liquid: $^1$H NMR δ2.7–2.8 (m, 2H), 3.3–3.5 (m, 4H), and 3.6–3.8 (m, 4H); C-13 NMR Γ177.6 (C=O), and 44.2, 52.9, 54.0, 63.0, and 63.4 representing 4 carbon atoms on two hydroxyethyl moieties and 1 methylene carbon atom on glycine moiety.

B) N,N''-bis[N''''-(2-hydroxyethyl)carbamoylmethyl-N'''-(2-hydroxyethyl)carbanoylmethyl]diethylenetriamine-N,N',N''-triacetic acid(7)

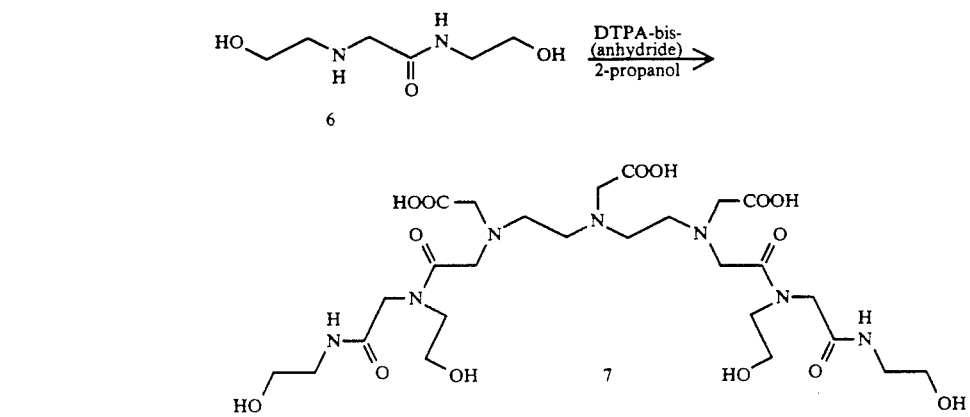

A slurry of 4.64 g (13.0 m mol) DTPA bisanhydride in 20 ml dry dimethyl formamide (DMF) was prepared. A solution of 4.0 g (24.7 m mol) of the secondary amine (6) in 15 ml dry DMF was added dropwise to it. The mixture was stirred at room temperature for 60 minutes and then at 55° C. for 2 hours. At the end of the reaction, 5 ml of water was added in order to digest the unreacted DTPA bisanhydride. The entire mixture was stirred at room temperature overnight. The solid formed (DTPA) was removed by filtration. The solvent was removed by rotary evaporation under reduced pressure. The DTPA bisamide (7) was purified from the residue by employing C-18 chromatography.

C) [N,N''-bis[N''''-(2-hydroxyethyl)carbamoylmethyl-N'''-(2-hydroxyethyl)carbamoylmethyl]diethylenetriamine-N,N',N''-triacetate]]gadolinium(III)(8)

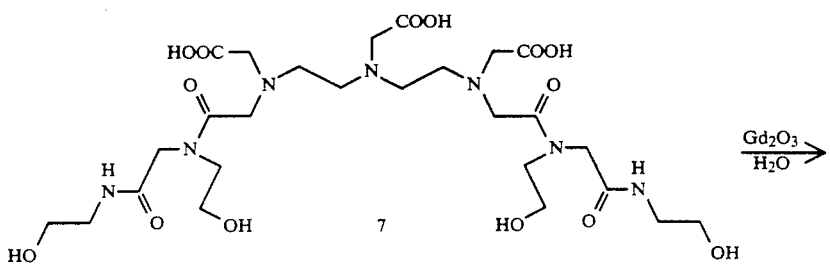

-continued

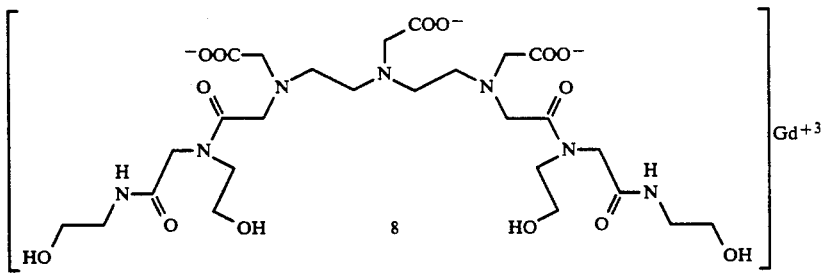

Gadolinium oxide (1.91 g, 5.27 m mol) was added to (7) (7.2 g, 10.6 m mol) in 50 ml of water. The mixture was stirred at 69°-71° C. overnight. The solution was filtered and water was removed by rotary evaporation. The crude product (8) (9.2 g, 103.4%) was a white powder.

As various changes could be made in the above compounds and methods without departing from the scope of the invention, it is intended that all matter contained in the above description or shown in the accompanying drawings shall be interpreted as illustrative and not in a limiting sense.

What is claimed is:

1. A diagnostic composition suitable for enteral or parenteral administration to a warm-blooded animal, which comprises an MRI-effective amount of a complex of a paramagnetic ion comprising the following formula:

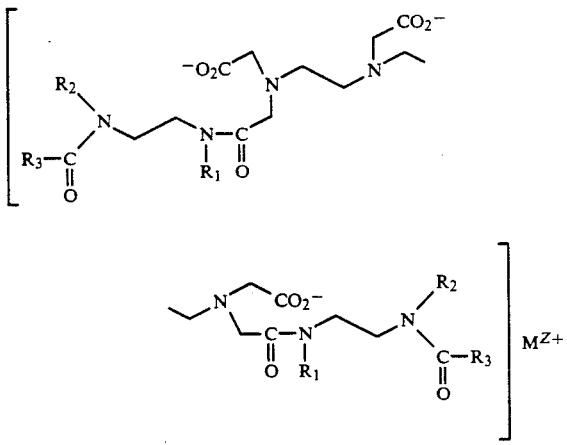

wherein the $R_1$, $R_2$ and $R_3$ groups may be the same or different selected from the group consisting of hydrogen, $C_{1-6}$ alkyl, $C_{1-6}$ alkoxy, $C_{1-6}$ monohydroxyalkyl, $C_{1-6}$ polyhydroxyalkyl, $C_{1-6}$ alkylalkoxy and $C_{1-6}$ alkoxyalkyl and $M^{2+}$ is a paramagnetic ion selected from a group of elements having atomic numbers of 21-25, 27-29, 42-44, and 58-70 and a valence, z, of 2+ or 3+; and a pharmaceutically acceptable carrier.

2. The diagnostic composition of claim 1 wherein $M^{2+}$ is chromium (III), manganese (II), manganese (III), iron (III), praseodymium (III), neodymium (III), samarium (III), ytterbium (III), gadolinium (III), terbium (III), dysprosium (III), holmium (III) or erbium (III).

3. The diagnostic composition of claim 1 wherein the complex is dissolved or suspended in a sterile aqueous pharmaceutically acceptable carrier at a concentration of from about 0.05 to 1.0 M.

4. The diagnostic composition of claim 1 which further contains a pharmaceutically acceptable buffer.

5. A method of performing a magnetic resonance imaging diagnostic procedure, which comprises administering to a warm-blooded animal an effective amountof a complex of the formula:

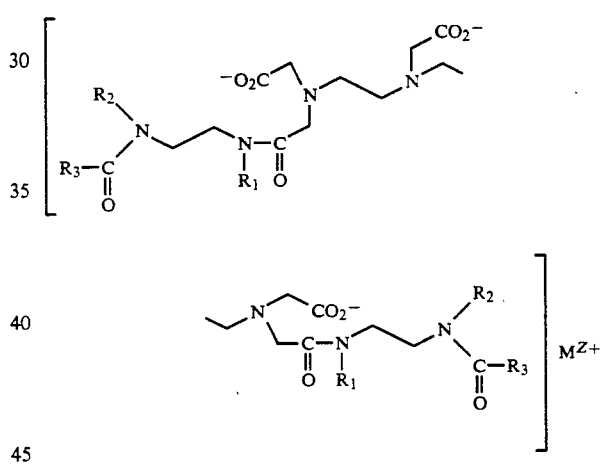

wherein the $R_1$, $R_2$ and $R_3$ groups may be the same or different selected from the group consisting of hydrogen, $C_{1-6}$ alkyl, $C_{1-6}$ alkoxy, $C_{1-6}$ monohydroxyalkyl, $C_{1-6}$ polyhydroxyalkyl, $C_{1-6}$ akylalkoxy and $C_{1-6}$ alkoxyalkyl; and $M^{2+}$ is aparamagnetic ion selected from a group of elements having atomic numbers of 21-25, 27-29, 42-44, and 58-70 and a valence, z, of 2+ or 3+; and then exposing the animal to a magnetic resonance imaging procedure, thereby imaging at least a portion of the body of the warm-blooded animal.

6. The method of claim 5 wherein $M^{2+}$ is chromium (III), manganese (II), manganese (III), iron (III), praseodymium (III), neodymium (III), samarium (III), ytterbium (III), gadolinium (III), terbium (III), dysprosium (III), holmium (III) or erbium (III).

* * * * *